United States Patent [19]
Schlecker et al.

[11] Patent Number: 5,612,344
[45] Date of Patent: Mar. 18, 1997

[54] TRIAZOLOQUINAZOLINES FOR THE TREATMENT OF CENTRAL NERVOUS DISORDERS

[75] Inventors: Rainer Schlecker, Bissersheim; Hans-Jörg Treiber, Bruehl; Berthold Behl, Ludwigshafen; Hans P. Hofmann, Limburgerhof, all of Germany

[73] Assignee: BASF Aktiengesellschaft, Ludwigshafen, Germany

[21] Appl. No.: 433,509

[22] PCT Filed: Dec. 6, 1993

[86] PCT No.: PCT/EP93/03424

§ 371 Date: May 12, 1995

§ 102(e) Date: May 12, 1995

[87] PCT Pub. No.: WO94/13294

PCT Pub. Date: Jul. 23, 1994

[30] Foreign Application Priority Data

Dec. 10, 1992 [DE] Germany .......................... 42 41 564.0

[51] Int. Cl.⁶ .................. A61K 31/505; C07D 487/02
[52] U.S. Cl. ................... 514/257; 514/267; 544/247; 544/251
[58] Field of Search .................... 544/247, 251; 514/257, 267

[56] References Cited

U.S. PATENT DOCUMENTS 4,463,007  7/1984  Schlecker et al. .................. 424/251
4,713,383  12/1987  Francis et al. .................... 514/267
5,153,196  10/1992  McQuaid et al. .................. 514/250

FOREIGN PATENT DOCUMENTS 080176  6/1983  European Pat. Off. .
181282  5/1986  European Pat. Off. .
1768116  10/1971  Germany .

OTHER PUBLICATIONS

Synthesis and Benzodiazepine Binding Activity of a Series of Novel . . . Francis et al., Am. Chem. So. 1991, pp. 281–290, vol. 34, No. 1.

Ligand: A Versatile Computerized Approach . . . , Analytical Biochemistry, vol. 107, pp. 220–239 (1980).

Primary Examiner—Matthew V. Grumbling
Attorney, Agent, or Firm—Keil & Weinkauf

[57] ABSTRACT

The use of triazoloquinazolines for the production of drugs for controlling central nervous disorders is described. The triazoloquinazolines have the formula

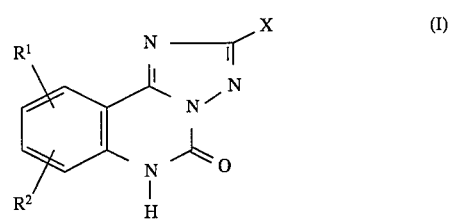

where $R^1$, $R^2$ and X have the meanings stated in the description.

4 Claims, No Drawings

TRIAZOLOQUINAZOLINES FOR THE TREATMENT OF CENTRAL NERVOUS DISORDERS

This is a national stage application filed under 35 USC 371 of PCT/EP93/03424, filed Dec. 6, 1993.

The present invention relates to the use of triazoloquinazolines for the treatment of central nervous disorders.

Triazoloquinazolines have been disclosed in EP-A 80 176. These compounds are reported to have an anti-allergic effect. It is furthermore known that certain pyrazoloquinazolines are suitable inter alia for the treatment of neurological disturbances (US-A 5 153 196).

The invention relates to the use of compounds of the formula I

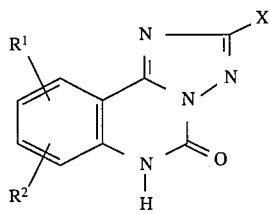

where

X is carboxyl, where appropriate in the form of its salt with a physiologically tolerated amine cation or metal cation; the radical

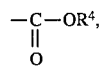

where $R^4$ is $C_{1-8}$-alkyl, cycloalkyl with 3 to 8 carbons in the ring, benzyl, one of the radicals

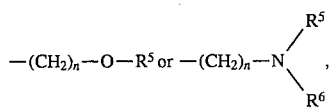

where n is 2, 3 or 4 and $R^5$ and $R^6$ are each $C_{1-3}$-alkyl; hydroxy-$C_{1-4}$-alkyl, nitrile-$C_{1-4}$-alkyl, tetrazolyl, carbonylaminotetrazole or carbamoyl, and $R^1$ and $R^2$, which are identical or different, and [sic] are hydrogen, fluorine, chlorine or bromine atoms, trifluoromethyl, nitro, amino, $C_{1-5}$-alkyl, mono- or di-$C_{1-5}$-alkylamino groups, a $C_{1-6}$-alkoxy group, a $C_{1-6}$-alkylthio, $C_{1-6}$-alkylsulfenyl, $C_{1-6}$-alkylsulfonyl, di-$C_{1-6}$-alkylaminosulfonyl radical, or $R^1$ and $R^2$ together form a methylene- or ethylenedioxy group or a $C_{3-5}$-alkylene group, and their physiologically tolerated acid addition salts for the production of drugs for the treatment of central nervous disorders.

Compounds of the formula I are described in EP-A 80 176. The latter also lists a large number of compounds which are also suitable for the novel indication.

Examples of relevant central nervous disorders are epilepsy, brain damage, Parkinson's disease, Alzheimer's disease, emesis, and trauma of the head and spinal cord. The compounds of the formula I have the further advantage that they have spasmolytic, antiepileptic, anxiolytic and antidepressant properties. The effect of the compounds derives from their glutamate-antagonistic properties.

The pharmacological activity of the compounds I according to the invention was investigated on isolated membrane material from rat cerebra. To do this, the membrane material was treated in the presence of the compounds according to the invention with the radiolabeled substances ³H-2-amino-3-hydroxy-5-methyl-4-isoxazolepropionic acid (³H-AMPA) and ³H-5,7-dichlorokynurenic acid, these binding to specific receptors (AMPA and NMDA (N-methyl-D-aspartate) receptors respectively). Subsequently the radioactivity on the treated membranes was measured by scintillation counting. The amounts of bound ³H-AMPA and ³H-5,7-dichlorokynurenic acid, or in each case the amounts of these radiolabeled substances displaced, were determined from the bound radioactivity. The dissociation constant $K_I$ (I=inhibitor) which results from this and which is a measure of the displacing effect of the active substance according to the invention was found by iterative non-linear regression analysis using the statistical analysis system (SAS) on an IBM computer similar to the "ligand" program of P. J. Munson and D. Rodbard (Analytical Biochem., 220 (1980) 107, Ligand: Versatile Computerized Approach for Characterization of Ligand Binding Systems).

The following in vitro investigations were carried out:

1. Binding of ³H-2-amino-3-hydroxy-5-methyl-4-isoxazolepropionic acid (³H-AMPA)

To prepare the membrane material, freshly removed rat cerebra were homogenized together with 15 times the volume of a buffer solution A composed of 30 mM α,α,α-tris(hydroxymethyl)methylamine hydrochloride (TRIS-HCl) and 0.5 mM ethylenediaminetetraacetic acid (EDTA), pH 7.4, using an Ultra-Turrax. The suspension was centrifuged at 4,000 g for 20 minutes. After removal of the supernatant liquid, the proteinacious membrane material contained in the sediment was washed three times by suspending it in buffer solution A and subsequently centrifuging at 48,000 g for 20 minutes each time. The membrane material was then suspended in 15 times the volume of buffer solution A and incubated at 37° C. for 30 minutes. The protein material was subsequently washed twice by centrifugation and suspension and stored at −70° C. until used.

For the binding assay, the protein material was thawed at 37° C. and washed twice by centrifuging at 48,000 g (20 minutes) and subsequently suspending in a buffer solution B composed of 50 mM TRIS-HCl, 0.1M potassium thiocyanate and 2.5 mM calcium chloride, pH 7.1. Subsequently 0.25 mg of membrane material, 0.1 μCi of ³H-AMPA (60 Ci/mmol) and compound I were dissolved in 1 ml of buffer solution B and incubated on ice for 60 minutes. The incubated solution was filtered through a CF/B filter (from Whatman) which had previously been treated for at least 2 hours with a 0.5% strength aqueous solution of polyethyleneimine. The filtrate was subsequently washed with 5 ml of cold buffer solution B in order to separate bound and free ³H-AMPA from one another. The radioactivity of the bound ³H-AMPA in the membrane material was measured by scintillation counting and then the $K_I$ was determined by subjecting the displacement plots to regression analysis.

The results were as follows:

| Substance | Ki [sic] [μM] |
|---|---|
| 8-Trifluoromethyl-1,2,4-triazolo[1,5-c]-quinazolin-5-one-2-carboxylic acid | 1.4 |
| 8,10-Dichloro-1,2,4-triazolo[1,5-c]-quinazolin-5-one-2-carboxylic acid | 1.3 |
| 8-Nitro-1,2,4-triazolo[1,5-c]-quinazolin-5-one-2-carboxylic acid | 2.6 |

2. Binding of ³H-5,7-dichlorokynurenic acid

To prepare the membrane material, freshly removed rat cerebra were homogenized together with about 10 times the volume of a buffer solution A composed of 50 mM TRIS-HCl and 10 mM EDTA, pH 7.4. The suspension was centrifuged at 48,000 g for 20 minutes. After removal of the supernatant liquid, the membrane material contained in the sediment was washed twice by suspending it in buffer solution A and subsequently centrifuging for 20 minutes each time. After resuspension of the membranes in buffer solution A and freezing in liquid nitrogen, the suspension was thawed again at 37° C. and, after another wash, incubated at 37° C. for 15 minutes. The protein material was subsequently washed four times by centrifugation and suspension and stored at −70° C. until used.

For the binding assay, the protein material was thawed at 37° C. and washed twice by centrifuging at 48,000 g (20 minutes) and subsequently suspending in a buffer solution B composed of 50 mM TRIS-HCl, pH 7.4. Subsequently 0.15 mg of membrane material, 0.3 µCi $^3$H-5,7-dichlorokynurenic acid (16 Ci/mmol) and compound I were dissolved in 1 ml of buffer solution B and incubated on ice for 30 minutes. The incubated solution was centrifuged at 150,000 g for 2 minutes. After removal of the supernatant liquid, the sediments were suspended twice using 1.5 ml of cold buffer solution B each time. The radioactivity of the $^3$H-5,7-dichlorokynurenic acid bound to the membranes in the sediment was measured, and the $K_I$ was obtained by subjecting the displacement plots to regression analysis.

The results were as follows:

| Substance | Ki [sic] [µM] |
|---|---|
| 8,9-Dimethyl-1,2,4-triazolo[1,5-c]-quinazolin-5-one-2-carboxylic acid | 0.09 |
| 8,10-Dichloro-1,2,4-triazolo[1,5-c]-quinazolin-5-one-2-carboxylic acid | 0.2 |
| Ethyl 8,9-dimethyl-1,2,4-triazolo-[1,5-c]-quinazolin-5-one-2-carboxylate | 0.16 |

The compounds I are suitable as active substances in drugs for human and veterinary medicine. The drug formulations contain a therapeutically effective amount of compound I in addition to conventional pharmaceutical ancillary substances.

The drug formulations can be administered in various ways such as orally, parenterally, subcutaneously, intraperitoneally and topically. Thus, possible presentations are tablets, emulsions, solutions for infusion and injection, pastes, ointments, gels, creams, lotions, dusting powders and sprays.

For local external use, e.g. in dusting powders and ointments, the active substances can be present in the conventional concentrations. The content of active substances is, as a rule, from 0.001 to 5% by weight, preferably from 0.01 to 0.5% by weight.

For internal use, the preparations are administered in single doses. From 0.1 to 50 mg, preferably from 0.1 to 10 mg, of active substance are given in a single dose per kg of body weight. The formulations can be administered in one or more dosages each day depending on the nature and severity of the disorder. The daily dose is, as a rule, from 0.1 to 100 mg per kg of body weight on oral administration and from 0.01 to 10 mg per kg of body weight on parenteral administration.

Besides the active substance, the drug formulations according to the invention contain conventional excipients and diluents appropriate for the required mode of administration. For local external use it is possible to employ pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Suitable for internal use are, for example, lactose, propylene glycol, ethanol, starch, talc and polyvinylpyrrolidone.

It is furthermore possible for antioxidants such as tocopherol and butylated hydroxyanisole as well as butylated hydroxytoluene, flavor-improving additives, stabilizers, emulsifiers and bleaches to be present.

The substances present in the formulation in addition to the active substance, as well as the substances used to produce the pharmaceutical formulation must be toxicologically acceptable and compatible with the active substance in each case.

The drug formulations are produced in a conventional way.

EXAMPLE 1

Tablets of the following composition are compressed in a tableting machine in a conventional way:

40 mg of 8,9-dimethyl-1,2,4-triazolo[1,5-c]quinazolin-5-one-2-carboxylic acid 120 mg of corn starch 13.5 mg of gelatin 45 mg of lactose 2.25 mg of Aerosil® (chemically pure silica in submicroscopically fine dispersion)

6.75 mg of potato starch (as 6% paste)

EXAMPLE 2

Coated tablets of the following composition are produced in a conventional way:

20 mg of 8,9-Dimethyl-1,2,4-triazolo[1,5-c]quinazolin-5-one-2-carboxylic acid 60 mg of core composition 60 mg of sugar-coating composition The core composition is composed of 9 parts of corn starch, 3 parts of lactose and 1 part of Luviskol® VA 64 (60:40 vinylpyrrolidone/vinyl acetate copolymer, cf. Pharm. Ind. 1962, 586). The sugar-coating composition is composed of 5 parts of sucrose, 2 parts of corn starch, 2 parts of calcium carbonate and 1 part of talc. The coated tablets produced in this way are subsequently provided with an enteric coating.

EXAMPLE 3

10 g of 8,9-dimethyl-1,2,4-triazolo[1,5-c]quinazolin-5-one-2-carboxylic acid are dissolved in 5000 ml of water with the addition of NaCl and the pH is adjusted to 6.0 with 0.1N NaOH to produce a solution which is isotonic with blood. 5 ml portions of this solution are dispensed into ampoules and sterilized.

We claim:

1. A process for treating central nervous disorders which comprises administering to a patient in need thereof an effect amount of a composition comprising a compound of the formula I

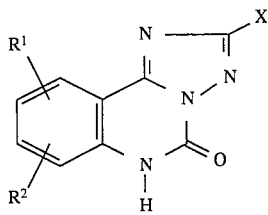

where

X is carboxyl, or carboxyl in the form of its salt with a physiologically tolerated amine cation or metal cation, the radical

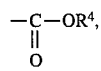

where $R^4$ is $C_{1-8}$-alkyl, cycloalkyl with 3 to 8 carbons in the ring, benzyl, one of the radicals

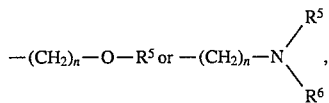

where n is 2, 3 or 4 and $R^5$ and $R^6$ are each $C_{1-3}$-alkyl; hydroxy-$C_{1-4}$-alkyl, nitrile-$C_{1-4}$-alkyl, tetrazolyl, carbonylaminotetrazole or carbamoyl, and $R^1$ and $R^2$, which are identical or different, and are hydrogen, fluorine, chlorine or bromine atoms, trifluoromethyl, nitro, amino, $C_{1-5}$-alkyl, mono- or di-$C_{1-5}$-alkylamino groups, a $C_{1-6}$-alkoxy group, a $C_{1-6}$-alkylthio, $C_{1-6}$-alkylsulfenyl, $C_{1-6}$-alkylsulfonyl, di-$C_{1-6}$-alkylaminosulfonyl radical, or $R^1$ and $R^2$ together form a methylene- or ethylenedioxy group or a $C_{3-5}$-alkylene group, and their physiologically tolerated acid addition salts, wherein said central nervous disorder is epilepsy, brain damage, Parkinson's disease, emesis or trauma of the head or spinal cord.

2. The process of claim 1 wherein the composition includes antioxidants.

3. The process of claim 1 wherein the composition is administered orally, parenterally, subcutaneously, intraperitoneally, or topically.

4. The process of claim 1 wherein the compound is 8,9-dimethyl-1,2,4-triazolo(1,5-c)quinazolin-5-one-2-carboxylic acid.

* * * * *

UNITED STATES PATENT AND TRADEMARK OFFICE
CERTIFICATE OF CORRECTION

PATENT NO.: 5,612,344

DATED: March 18, 1997

INVENTOR(S): SCHLECKER et al.

It is certified that error appears in the above-identified patent and that said Letters Patent is hereby corrected as shown below:

On the cover page, item [87], the PCT Pub. Date "Jul. 23, 1994" should be --Jun. 23, 1994--

Signed and Sealed this

Twenty-seventh Day of May, 1997

Attest:

BRUCE LEHMAN

Attesting Officer

Commissioner of Patents and Trademarks